United States Patent

Rovati et al.

[11] 4,288,609
[45] Sep. 8, 1981

[54] QUATERNARY AMMONIUM DERIVATIVES OF ADAMANTANE WITH ANTIMICROBIC ACTIVITY

[75] Inventors: Luigi Rovati, San Fruttuoso di Monza; Francesco Makovec, Taccona; Paolo Senin, Monza, all of Italy

[73] Assignee: Rotta Research Laboratorium S.p.A., San Fruttuoso di Monza, Italy

[21] Appl. No.: 100,065

[22] Filed: Dec. 4, 1979

Related U.S. Application Data

[63] Continuation of Ser. No. 853,591, Nov. 21, 1977, abandoned.

[30] Foreign Application Priority Data

Nov. 24, 1976 [IT] Italy .................. 69791 A/76

[51] Int. Cl.³ ............... C07C 67/08; C07C 102/04
[52] U.S. Cl. .................... 560/117; 564/138; 564/188; 424/299; 424/320
[58] Field of Search .............. 260/567.6 M; 560/117; 564/138, 292

[56] References Cited

U.S. PATENT DOCUMENTS 3,342,840  9/1967  Sobalor .................. 260/567.6 M
3,907,895  9/1975  Bauman .................. 260/567.6 M
3,928,411 12/1975  Bauman .................. 260/567.6 M

OTHER PUBLICATIONS

Fieser et al., Reagents for Organic Synthesis, pp. 231–234 (1966).
Buzas et al., Compt. Rend, #252, pp. 896–898 (1961).
Buzas et al., Compt. Rend, #255, pp. 945–947 (1962).
Stempel et al., J. Org. Chem., vol. 27, pp. 4671–4672 (1962).

Primary Examiner—Natalie Trousof
Assistant Examiner—James H. Reamer
Attorney, Agent, or Firm—Sughrue, Mion, Zinn, Macpeak and Seas

[57] ABSTRACT

Compounds having the general formula:

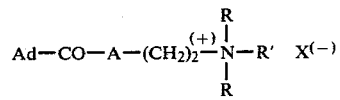

in which:
Ad is 1-adamantyl ($C_{10}H_{15}$) radical
A is oxygen atom or —NH—(imino) group
R is —$CH_3$ (methyl) group or —$C_2H_5$ (ethyl) group
R' is a linear aliphatic chain containing from 10 to 12 atoms of carbon
$X^-$ is a halide ion.

The halide may be chlorine or bromine. The compounds exhibit an antibacterial, antimould and antiprotozoic activity and may be formulated as pharmaceutical and cosmetic preparations or used as preservatives for food products.

3 Claims, No Drawings

QUATERNARY AMMONIUM DERIVATIVES OF ADAMANTANE WITH ANTIMICROBIC ACTIVITY

This is a Continuation, of application Ser. No. 853,591, filed Nov. 21, 1977, now abandoned.

The present invention relates to a series of new quaternary ammonium derivatives with antibacterial, antimould and antiprotozoic activity.

The use of quaternary ammonium salts as disinfectants is known, both in the surgical field and in the local treatment of cutaneous and mucous infections.

One of the main disadvantages of this class of substances is their relatively high general toxicity coupled with a certain local irritative action which greatly restricts its use in human therapy. Other disadvantages of the quaternary ammonium derivatives are the long period of time needed for germicidal action, and their partial inactivation in the presence of serum or various proteins, which renders the result of their practical use uncertain.

These disadvantages are obviated by the compounds of the present invention which have shown to possess characteristics which ensure favourable use in the local treatment of microbic infections in man or in animals and in the protection of foodstuffs against contamination and of any other matter which might be damaged by micro-organisms.

The quaternary ammonium compounds according to the invention may be represented by the following general formula:

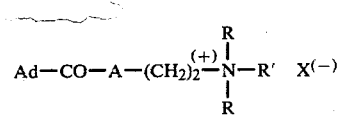

in which
Ad is the 1-adamantyl ($C_{10}H_{15}$) radical,

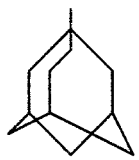

A is oxygen atom or —NH— (imino) group,
R is —CH$_3$ (methyl) or —C$_2$H$_5$ (ethyl) group,
R' is a linear aliphatic chain containing from 10 to 12 atoms of carbon,
X$^-$ is a halide ion such as chloride (Cl$^-$) or bromide (Br$^-$).

The compounds can with advantage be prepared in a single passage according to the synthesis scheme given below:

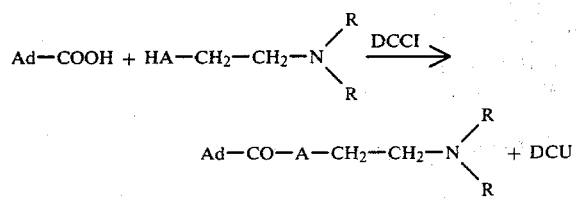

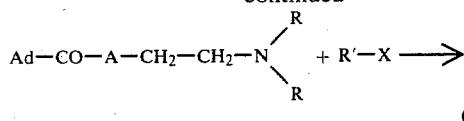

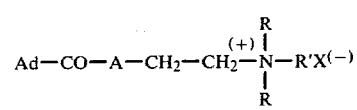

The process comprises reacting 1-carboxyadamantane with stoichiometric quantity of the appropriate dialkylaminoethylamine or of the corresponding dialkylaminoethanol in the presence of an excess of a condensation agent (1.3 moles), such as dicylohexylcarbodiimide (DCCI) or carbonyl di-imidazole, in an anhydrous non-hydroxylated organic solvent, such as dioxane, acetone, tetrahydrofuran, acetonitrile, ethyl acetate, chloroform, dichloromethane, during a time from 12 to 48 hours (preferably 24) and at a temperature from 5° C. to 30° C. (typically 20°).

The intermediate compound (I) is not isolated from the reaction medium, but rather, after elimination by filtration of the dicyclohexylurea (DCU) which has been formed and precipitated during the condensation it is reacted to form the quaternary salt in the same solvent with a slight excess (1.1 moles) of the appropriate alkyl halide at a temperature which corresponds to the boiling point of the solvent used, and during a period of time varying from 8 to 24 hours (typically 18).

When the reaction is terminated the product is separated from the reaction medium in crystalline form, simply by cooling or by concentration of the solvent. After filtration and drying the product does not need further treatments since it is free from impurities.

EXAMPLE 1 n-Decyl-dimethyl-(1-adamantane-carboxy)-ethyl-ammonium bromide

A solution of 18.02 g (0.1 moles) of 1-carboxyadamantane and 10 cc (0.1 moles) of dimethylaminoethanol in 200 cc of anhydrous acetone is additioned under agitation and at a temperature of 5° C., with 26.8 g (0.13 moles) of dicyclohexylcarbodiimide; after about 20 minutes a crystalline precipitate of dicyclohexylurea begins to separate and the precipitation increases progressively. At this point the temperature is brought to 20° C. and agitation is continued for 24 hours.

The dicyclohexylurea formed in the course of the reaction is separated by filtration, whilst the residual acetone solution containing the product (I) is additioned with 22.9 cc (0.11 moles) of 1-bromodecane and is refluxed for 18 hours. After cooling the solution to 0° C. an abundant brilliant-white crystalline mass is precipitated, which is filtered, washed with isopropyl ether and dried at 50° C.

Product: g 43.7, Yield: 92.6%, m.p.: 182°–184° C.

| Microanalysis ($C_{25}H_{46}BrNO_2$) | | | | |
|---|---|---|---|---|
| | C% | H% | N% | Br% |
| Calc. | 64.77 | 10.00 | 3.02 | 17.24 |
| Found | 64.39 | 9.87 | 3.00 | 17.05 |

EXAMPLE 2 n-Decyl-dimethyl-(1-adamantane-carboxy)-ethyl-ammonium chloride

The procedure is as in Example 1, using 22.4 cc (0.11 moles) of 1-chlorodecane instead of 1-bromodecane.
Product: 34.67 g, Yield: 81.0%, m.p.: 178°–180° C.

| | Microanalysis ($C_{25}H_{46}ClNO_2$) | | | |
|---|---|---|---|---|
| | C% | H% | N% | Cl% |
| calc. | 70.14 | 10.83 | 3.27 | 8.28 |
| found | 69.58 | 10.34 | 3.18 | 8.17 |

EXAMPLE 3 n-Undecyl-dimethyl-(1-adamantane-carboxy)methyl-ammonium bromide

The procedure is as in Example 1, using 24.6 cc (0.11 moles) of 1-bromo-undecane instead of 1-bromodecane.
Product: 42.09 g, Yield: 86.5%, m.p.: 176°–179° C.

| | Microanalysis ($C_{26}H_{48}NO_2Br$) | | | |
|---|---|---|---|---|
| | C% | H% | N% | Br% |
| calc. | 64.18 | 9.94 | 2.88 | 16.42 |
| found | 64.02 | 9.87 | 2.81 | 16.47 |

EXAMPLE 4 n-Dodecyl-dimethyl-(1-adamantane-carboxy)-methyl-ammonium bromide

The procedure is as in Example 1, using 26.5 cc (0.11 moles) of 1-bromododecane instead of 1-bromodecane.
Product: 45.8 g, Yield: 91.5%, m.p.: 171°–173° C.

| | Microanalysis ($C_{27}H_{50}BrNO_2$) | | | |
|---|---|---|---|---|
| | C% | H% | N% | Br% |
| calc. | 64.78 | 10.07 | 2.80 | 15.96 |
| found | 64.51 | 9.97 | 2.76 | 15.84 |

EXAMPLE 5 n-Decyl-diethyl-(1-adamantane-carboxy)-ethyl-ammonium bromide

The procedure is as in Example 1, using 13.23 cc (0.1 moles) of diethylaminoethanol instead of dimethylaminoethanol.
Product: 41.6 g, Yield: 83.1%, m.p.: 165°–168° C.

| | Microanalysis ($C_{27}H_{50}BrNO_2$) | | | |
|---|---|---|---|---|
| | C% | H% | N% | Br% |
| calc. | 64.78 | 10.07 | 2.80 | 15.96 |
| found | 64.62 | 9.98 | 2.71 | 15.87 |

EXAMPLE 6 n-Dodecyl-diethyl-(1-adamantane-carboxy)-ethyl-ammonium bromide

The procedure is as in Example 4 using 13.23 cc (0.1 moles) of dietylaminoethanol instead of dimethylaminoethanol.
Product: 42.7 g, Yield: 80.7%, m.p.: 155°–157° C.

| | Microanalysis ($C_{29}H_{54}BrNO_2$) | | | |
|---|---|---|---|---|
| | C% | H% | N% | Br% |
| calc. | 66.07 | 10.30 | 2.65 | 15.11 |
| found | 65.89 | 10.19 | 2.57 | 15.03 |

EXAMPLE 7 n-Decyl-dimethyl-(1-adamantane-carbonylamido)-methyl-ammonium bromide

A solution of 18.02 g (0.1 moles) of 1-carboxy-adamantane and 10.9 cc (0.1 moles) of dimethylaminoethylamine in 250 cc of anhydrous acetonitrile, is additioned under agitation and at a temperature of 0° C. with 26.8 g (0.13 moles) of dicyclohexylcarbodiimide; almost immediately a crystalline precipitate of dicyclohexylurea starts to separate and increases progressively. At this point the temperature is brought to 20° C. and agitation is continued for 24 hours.

The dicyclohexylurea which has formed in the course of the reaction is separated by filtration whilst the solution of the product (I) in acetonitrile is additioned with 22.9 cc (0.1 moles) of 1-bromodecane and is refluxed for 18 hours.

The solution is concentrated under vacuum until a final volume of 150 cc is obtained; by leaving it at 0° C. the product crystallises in the form of brilliant-white platelets and is filtered, washed with isopropyl ether and dried at 50° C.
Product: 43.05 g, Yield: 91.3%, m.p.: 122°–125° C.

| | Microanalysis ($C_{25}H_{47}BrN_2O$) | | | |
|---|---|---|---|---|
| | C% | H% | N% | Br% |
| calc. | 63.68 | 10.05 | 5.94 | 16.95 |
| found | 63.41 | 9.96 | 5.87 | 16.81 |

EXAMPLE 8 n-Dodecyl-dimethyl-(1-adamantane-carbonylamido)-methylammonium bromide

The procedure is as in Example 7 using 26.5 cc (0.11 moles) of 1-bromododecane instead of 1-bromodecane.
Product: 45.25 g, Yield: 90.6%, m.p. 135°–137° C.

| | Microanalysis ($C_{27}H_{51}BrN_2O$) | | | |
|---|---|---|---|---|
| | C% | H% | N% | Br% |
| calc. | 64.90 | 10.30 | 5.61 | 15.99 |
| found | 64.72 | 10.21 | 5.49 | 15.83 |

EXAMPLE 9 n-Decyl-diethyl-(1-adamantane-carbonylamido)-ethylammonium bromide

The procedure is as in example 7 using 14.2 cc (0.1 moles) of diethylaminoethylamine instead of dimethylaminoethylamine.
Product: 44.51 g, Yield: 89.1%, m.p. 165°–168° C.

| | Microanalysis ($C_{27}H_{51}Br\ NO_2O$) | | | |
|---|---|---|---|---|
| | C% | H% | N% | Br% |
| calc. | 64.90 | 10.30 | 5.61 | 15.99 |

-continued

| Microanalysis ($C_{27}H_{51}Br\ N_2O$) | | | | |
|---|---|---|---|---|
| | C% | H% | N% | Br% |
| found | 64.67 | 10.19 | 5.54 | 15.78 |

EXAMPLE 10 n-Decyl-diethyl-(1-adamantane-carbonylamido)-ethyl-ammonium chloride

The procedure is as in Example 9, using 22.4 cc (0.11 moles) of 1-chlorodecane instead of 1-bromodecane. Product: 38.05 g, Yield: 83.6%, m.p. 161°–163° C.

| Microanalysis ($C_{27}H_{51}Cl\ N_2O$) | | | | |
|---|---|---|---|---|
| | C% | H% | N% | Cl% |
| calc. | 71.24 | 11.29 | 6.15 | 7.79 |
| found | 70.98 | 11.19 | 6.07 | 7.73 |

EXAMPLE 11 n-Undecyl-diethyl-(1-adamantane-carbonylamido)-ethylammonium bromide

The procedure is as in Example 9, using 24.6 cc (0.11 moles) of 1-bromoundecane instead of 1-bromodecane. Product: 43.35 g, Yield 84.4%, m.p. 159°–160° C.

| Microanalysis ($C_{28}H_{53}Br\ N_2O$) | | | | |
|---|---|---|---|---|
| | C % | H % | N % | Br % |
| calc. | 65.47 | 10.40 | 5.45 | 15.56 |
| found | 65.17 | 10.29 | 5.40 | 15.42 |

EXAMPLE 12 n-Dodecyl-diethyl-(1-adamantane-carbonylamido)-ethylammonium bromide

The procedure is as in Example 9, using 26.5 cc (0.11 moles) of 1-bromododecane instead of 1-bromodecane.

Product: 45.33 g, Yield: 85.9%, m.p. 151°–154° C.

| Microanalysis ($C_{29}H_{55}Br\ N_2O$) | | | | |
|---|---|---|---|---|
| | C % | H % | N % | Br % |
| calc. | 66.01 | 10.51 | 5.31 | 15.15 |
| found | 65.86 | 10.42 | 5.26 | 15.04 |

A.: ACTIVITY IN VITRO $A_1$: On gram+ and gram− bacteria

The presence of the adamantane radical in the molecule of the products subject of this invention confers them, in addition to a very rapid sterilising action even at low concentration, other properties which generally do not appear all together in the characteristics of quaternary ammonium compounds used as disinfectants. These are a low toxicity, which is an indispensable element for practical utilisation without danger, a perfect cutaneous and mucous tolerability, which makes topical administration of these products possible even for long periods, and a very restrained seric inactivation, allows the use of the products at very low concentrations.

The method for evaluating the activity in vitro against bacteria, fungi and protozoa consists in introducing calculated quantities of the substance, the activity of which it is desired to test, into culture media already inoculated with a predetermined number of test germs.

After 24 or 48 hours of incubation at 30° or 37° C., according to the micro-organism being tested, it is possible to evaluate the growth of the same in the culture broth; in this manner the minimum concentration (M.I.C.) which inhibits the growth of the micro-organisms in vitro is determined.

In table 1 there are recorded the M.I.C. values in γ/ml of the products subject of the present invention, against certain gram+ and gram− bacterial strains, some of which are pathogenic towards human beings.

TABLE 1

| | | | | | BACTERIAL STRAIN GRAM+ | | | | | |
|---|---|---|---|---|---|---|---|---|---|---|
| | | | | | Staph.Aureus Tour | | Diplococcus Pneum. ISM | | Streptococ. Henclyt. 0203 | |
| | SUBSTITUENTS | | | | | +10% | | +10% | | +10% |
| COMPOUNDS | A | R | $R_1$ | X | — | serum | — | serum | — | serum |
| Example 1 | —O— | —$CH_3$ | —$C_{10}H_{21}$ | Br | <0.1 | 2 | 1 | 5 | <0.1 | 0.1 |
| Example 2 | —O— | —$CH_3$ | —$C_{10}H_{21}$ | Cl | 0.2 | 5 | 2 | 10 | 0.2 | 1 |
| Example 3 | —O— | —$CH_3$ | —$C_{11}H_{23}$ | Br | <0.1 | 5 | 0.5 | 5 | <0.1 | 9.2 |
| Example 4 | —O— | —$CH_3$ | —$C_{12}H_{25}$ | Br | <0.1 | 5 | 0.5 | 5 | <0.1 | 0.3 |
| Example 5 | —O— | —$C_2H_5$ | —$C_{10}H_{21}$ | Br | <0.1 | 5 | 0.5 | 10 | <0.1 | 0.5 |
| Example 6 | —O— | —$C_2H_5$ | —$C_{12}H_{25}$ | Br | 0.1 | 10 | 2 | 5 | 0.5 | 2 |
| Example 7 | —NH— | —$CH_3$ | —$C_{10}H_{21}$ | Br | 0.2 | 5 | 0.5 | 10 | 0.2 | 2 |
| Example 8 | —NH— | —$CH_3$ | —$C_{12}H_{25}$ | Br | <0.1 | 5 | 1 | 5 | <0.1 | 1 |
| Example 9 | —NH— | —$C_2H_5$ | —$C_{10}H_{21}$ | Br | 0.1 | 5 | 1 | 5 | 0.1 | 0.5 |
| Example 10 | —NH— | —$C_2H_5$ | —$C_{10}H_{21}$ | Cl | 0.2 | 10 | 2 | 10 | 0.5 | 5 |
| Example 11 | —NH— | —$C_2H_5$ | —$C_{11}H_{23}$ | Br | <0.1 | 10 | 1 | 5 | <0.1 | 2 |
| Example 12 | —NH— | —$C_2H_5$ | —$C_{12}H_{25}$ | Br | 0.2 | 10 | 2 | 20 | 0.2 | 5 |
| Cetyl-Pyridine Chloride | — | — | — | — | 0.1 | 10 | 1 | 10 | 0.5 | 5 |

| | | | | | BACTERIAL STRAIN GRAM− | | | | | | |
|---|---|---|---|---|---|---|---|---|---|---|---|
| | | | | | Esch. Coli. SKF 12140 | | Klens. Pneum. ISM | | Proteus Vulc. ATCC 881 | | Pseudom.Aer. ATCC 1014 |
| | SUBSTITUENTS | | | | | +10% | | +10% | | +10% | | +10% |
| COMPOUNDS | A | R | $R_1$ | X | — | serum | — | serum | — | serum | — | serum |
| Example 1 | —O— | —$CH_3$ | —$C_{10}H_{21}$ | Br | 5 | 50 | 5 | 50 | 10 | 50 | 20 | 50 |

TABLE 1-continued

| | A | R | $R_1$ | X | | | | | | | | |
|---|---|---|---|---|---|---|---|---|---|---|---|---|
| Example 2 | —O— | —CH$_3$ | —C$_{10}$H$_{21}$ | Cl | 10 | 100 | 20 | 100 | 20 | 100 | 50 | 100 |
| Example 3 | —O— | —CH$_3$ | —C$_{11}$H$_{23}$ | Br | 2 | 100 | 5 | 100 | 5 | 100 | 20 | 100 |
| Example 4 | —O— | —CH$_3$ | —C$_{12}$H$_{25}$ | Br | 2 | 100 | 2 | 100 | 2 | 100 | 10 | 100 |
| Example 5 | —O— | —C$_2$H$_5$ | —C$_{10}$H$_{21}$ | Br | 5 | 100 | 10 | 100 | 10 | 100 | 50 | 100 |
| Example 6 | —O— | —C$_2$H$_5$ | —C$_{12}$H$_{25}$ | Br | 10 | 100 | 10 | 100 | 20 | 100 | 50 | 100 |
| Example 7 | —NH— | —CH$_3$ | —C$_{10}$H$_{21}$ | Br | 10 | 100 | 10 | 50 | 10 | 100 | 50 | 100 |
| Example 8 | —NH— | —CH$_3$ | —C$_{12}$H$_{25}$ | Br | 2 | 100 | 5 | 50 | 5 | 100 | 10 | 50 |
| Example 9 | —NH— | —C$_2$H$_5$ | —C$_{10}$H$_{21}$ | Br | 5 | 50 | 10 | 50 | 5 | 100 | 10 | 50 |
| Example 10 | —NH— | —C$_2$H$_5$ | —C$_{10}$H$_{21}$ | Cl | 10 | 100 | 10 | 100 | 10 | 100 | 50 | >100 |
| Example 11 | —NH— | —C$_2$H$_5$ | —C$_{11}$H$_{23}$ | Br | 5 | 100 | 5 | 100 | 10 | 100 | 20 | 100 |
| Example 12 | —NH— | —C$_2$H$_5$ | —C$_{12}$H$_{25}$ | Br | 10 | 100 | 5 | 100 | 5 | 100 | 20 | 100 |
| Cetyl-Pyridine Chloride | — | — | — | — | 5 | >100 | 5 | >100 | 20 | >100 | 200 | >200 |

The results recorded in Table 1 demonstrate that the substances in question, and especially the compounds described in Example 1, 4 and 8 exert a powerful antibacterial activity at low concentrations, both upon gram positive strains and on gram negative strains. The seric inactivation is very limited and in any case such as not to inhibit the appearance of the germicidal effect.

This fact is made particularly evident by comparing the substances under examination with cetyl pyridine chloride, one of the quaternary ammonium salts best known and used in the field of local disinfection. It can in fact be noted that the activity of cetyl pyridine chloride against gram negative strains is practically imperceptible if tested in the presence of serum, whilst the quaternary ammonium salts described in the present invention manage to exert their activity equally even if a certain amount of inactivation is indisputably present. The differences are less marked in the case of the gram+ strains which are well known to be very sensitive to the action of the quaternary ammonium salts, but are still such as to confirm a more limited seric deactivation for the substances described in the present application.

A$_2$: Upon mildews, yeasts and protozoa

In order to confirm the wide spectrum of action of the compounds in question, their activity was also assessed against fungi (both mildews and yeasts) and protozoa, in this case also taking cetyl pyridine chloride as the standard substance.

Inoculation with *Candida albicans* or *Candida pseudotropicalis* was made by diluting cultures grown for 24 h at 30° C. (cellular density inoculated 10$^3$/ml).

Inoculation with *Trichophyton mentagrophytes* and *Microsporum canis* was effected in a ratio of 1% of the volume of medium used.

Inoculation with *Trichomonas vaginalis* and *Trichomonas foetus*, obtained from cultures transplanted every other day to make them lively, was effected in a ratio of 3.5% of the volume of medium used.

For the fungi Sabourand broth was used as a culture medium, whilst for the protozoa Kupferberg Trichomonas broth with 5% of horse serum was used. The results (MIC values in γ/ml) are recorded in Table 2.

TABLE 2

| | SUBSTITUENTS | | | | MILDEWS | | | |
|---|---|---|---|---|---|---|---|---|
| | | | | | Trych. Mentagr. 1st.Pastuer | | Nicrosporum Canis ATCC 11621 | |
| COMPOUNDS | A | R | $R_1$ | X | — | +10% serum | — | +10% serum |
| Example 1 | —O— | —CH$_3$ | —C$_{10}$H$_{21}$ | Br | 0.1 | 5 | 0.1 | 10 |
| Example 2 | —O— | —CH$_3$ | —C$_{10}$H$_{21}$ | Cl | 0.5 | 20 | 0.5 | 20 |
| Example 3 | —O— | —CH$_3$ | —C$_{11}$H$_{23}$ | Br | 0.1 | 10 | <0.1 | 10 |
| Example 4 | —O— | —CH$_3$ | —C$_{12}$H$_{25}$ | Br | 0.1 | 5 | 0.1 | 20 |
| Example 5 | —O— | —C$_2$H$_5$ | —C$_{10}$H$_{21}$ | Br | 0.1 | 10 | 0.1 | 20 |
| Example 6 | —O— | —C$_2$H$_5$ | —C$_{12}$H$_{25}$ | Br | 0.5 | 20 | 0.5 | 50 |
| Example 7 | —NH— | —CH$_3$ | —C$_{10}$H$_{21}$ | Br | 0.5 | 20 | 0.5 | 20 |
| Example 8 | —NH— | —CH$_3$ | —C$_{12}$H$_{25}$ | Br | 0.1 | 5 | 0.1 | 20 |
| Example 9 | —NH— | —C$_2$H$_5$ | —C$_{10}$H$_{21}$ | Br | 0.2 | 10 | 0.2 | 20 |
| Example 10 | —NH— | —C$_2$H$_5$ | —C$_{10}$H$_{21}$ | Cl | 0.5 | 50 | 0.5 | 50 |
| Example 11 | —NH— | —C$_2$H$_5$ | —C$_{11}$H$_{23}$ | Br | 0.1 | 10 | 0.2 | 20 |
| Example 12 | —NH— | —C$_2$H$_5$ | —C$_{12}$H$_{25}$ | Br | 0.2 | 20 | 0.5 | 20 |
| Cetyl Pyridine Chloride | — | — | — | — | 0.5 | 30 | 0.5 | 50 |

| | SUBSTITUENTS | | | | YEASTS | | | | PROTOZOA | | | |
|---|---|---|---|---|---|---|---|---|---|---|---|---|
| | | | | | Candida Albic. SKF 2270 | | Candida Pseudotrop. ATCC 2512 | | Trich. Vaginalis ISM 66/22 | | Trich. Foetus ISM 66/23 | |
| COMPOUNDS | A | R | $R_1$ | X | — | +10% serum | — | +10% serum | — | +10% serum | — | +10% serum |
| Example 1 | —O— | —CH$_3$ | —C$_{10}$H$_{21}$ | Br | 0.2 | 10 | <0.1 | 20 | — | 5 | — | 2 |
| Example 2 | —O— | —CH$_3$ | —C$_{10}$H$_{21}$ | Cl | 5 | 50 | 0.5 | 50 | — | 20 | — | 10 |
| Example 3 | —O— | —CH$_3$ | —C$_{11}$H$_{23}$ | Br | 0.5 | 20 | <0.1 | 50 | — | 5 | — | 5 |
| Example 4 | —O— | —CH$_3$ | —C$_{12}$H$_{25}$ | Br | 0.2 | 20 | 0.1 | 50 | — | 5 | — | 5 |
| Example 5 | —O— | —C$_2$H$_5$ | —C$_{10}$H$_{21}$ | Br | 0.5 | 50 | 0.1 | 50 | — | 10 | — | 5 |
| Example 6 | —O— | —C$_2$H$_5$ | —C$_{12}$H$_{25}$ | Br | 2 | 50 | 0.5 | 50 | — | 10 | — | 5 |
| Example 7 | —NH— | —CH$_3$ | —C$_{10}$H$_{21}$ | Br | 5 | 50 | 0.2 | 50 | — | 5 | — | 2 |
| Example 8 | —NH— | —CH$_3$ | —C$_{12}$H$_{25}$ | Br | 0.2 | 20 | <0.1 | 20 | — | 2 | — | 1 |

TABLE 2-continued

| | | | | | | | | | | | | |
|---|---|---|---|---|---|---|---|---|---|---|---|---|
| Example 9 | —NH— | —$C_2H_5$ | —$C_{10}H_{21}$ | Br | 1 | 20 | 0.2 | 50 | — | 5 | — | 2 |
| Example 10 | —NH— | —$C_2H_5$ | —$C_{10}H_{21}$ | Cl | 0.5 | 50 | 2 | 50 | — | 10 | — | 5 |
| Example 11 | —NH— | —$C_2H_5$ | —$C_{11}H_{23}$ | Br | 1 | 20 | <0.1 | 20 | — | 5 | — | 5 |
| Example 12 | —NH— | —$C_2H_5$ | —$C_{12}H_{25}$ | Br | 1 | 20 | 0.1 | 50 | — | 5 | — | 5 |
| Cetyl Pyridine Chloride | — | — | — | — | 5 | 100 | 0.5 | 100 | — | 10 | — | 5 |

By examining Table 2 it can be seen that the compounds under examination exert their antimicrobic action at very low concentrations, both upon fungi (yeasts and mildews) and upon protozoa.

Especially interesting is the activity on *Candida albicans*, a yeast which is responsible for harmful and resistant infections in man; this activity in the case of the more active products of the series (see Examples 1, 4, 8) is about 25 times greater than that of cetyl pyridine chloride in the absence of serum and 5–10 times higher in the presence of 10% of horse serum; the differences are less noticeable in the case of mildews and protozoa, but nevertheless such as to make apparent both the wide spectrum of the action and the superiority of the substances examined with respect to terms of comparison (cetyl pyridine chloride).

$A_3$: Speed of sterilising action

A very important element in the evaluation of an antimicrobic substance is the speed of its action; for this reason the time taken by a few of the more active compounds which are the subject of the present invention, to inhibit the growth of various micro-organisms was tested, their concentration being varied, and cetyl pyridine chloride was further taken into account as a term of comparison.

The strains, inoculants, culture broths and experimental methods are as already seen for calculating the M.I.C. in vitro. The antimicrobic substances were tested at concentrations of 0.1, 0.25, 0.5 and 1 g/l, the contact times taken into consideration are 0, 1, 2.5, 5, 7.5, 10, 15, 30 and 60 minutes.

The samples which at the 7th day of incubation still had no growth of micro-organisms which could be observed macroscopically and/or microscopically were considered sterile.

The results are recorded in Table 3 in terms of sterilization time expressed in minutes.

TABLE 3

| | | COMPOUNDS | | | | | | | | | | | | | | | |
|---|---|---|---|---|---|---|---|---|---|---|---|---|---|---|---|---|---|
| | | Example 1 (g/l) | | | | Example 4 (g/l) | | | | Example 8 (g/l) | | | | Cetyl Pyridine chlor. g/l | | | |
| MICRO-ORGANISMS | Strain | 0.1 | 0.25 | 0.5 | 1 | 0.1 | 0.25 | 0.5 | 1 | 0.1 | 0.25 | 0.5 | 1 | 0.1 | 0.25 | 0.5 | 1 |
| Bacteria | | | | | | | | | | | | | | | | | |
| Gram+ | | | | | | | | | | | | | | | | | |
| *Staphylococcus Aureus* | Tour | 7.5 | 2.5 | 1 | 1 | 7.5 | 5 | 1 | 1 | 7.5 | 5 | 2.5 | 1 | 7.5 | 2.5 | 1 | 1 |
| Gram— | | | | | | | | | | | | | | | | | |
| *Escherichia Coli* | SKF 12140 | 60 | 60 | 15 | 5 | 60 | 60 | 30 | 10 | 60 | 60 | 10 | 7.5 | >60 | >60 | >60 | >60 |
| Fungi | | | | | | | | | | | | | | | | | |
| Mildews | | | | | | | | | | | | | | | | | |
| *Trichophyton Mentagrophytes* | Ist. Pasteur | 60 | 30 | 15 | 5 | 60 | 60 | 15 | 5 | 60 | 60 | 10 | 5 | 60 | 60 | 30 | 5 |
| Yeasts | | | | | | | | | | | | | | | | | |
| *Candida Albicans* | SKF 2270 | 30 | 2.5 | 1 | 1 | 30 | 10 | 5 | 1 | 60 | 15 | 2.5 | 2.5 | 60 | 10 | 10 | 10 |
| Protozoa | | | | | | | | | | | | | | | | | |
| *Trichomonas Vaginalis* | ISM 66/22 | 2.5 | 1 | 1 | 1 | 2.5 | 1 | 1 | 1 | 2.5 | 1 | 1 | 1 | 5 | 2.5 | 1 | 1 |

The results recorded in Table 3 make it apparent that the substances described in Examples 1, 4, 8, exert a swift sterilising action on all the micro-organisms tested even with a very low concentration.

This fact confirms the wide spectrum of action of the compounds being tested and a very high speed of sterilisation even on micro-organisms which are generally very resistant, such as gram negative bacteria and yeasts.

It is interesting to emphasize that cetyl pyridine chloride even in the very high concentration tested is not capable of exerting its action on Escherichia coli, whilst it acts rather slowly on Candida Albicans. On the other hand the compounds of the present invention, as we have seen, act swiftly and radically upon these micro-organisms.

B.: TOXICITY

The acute oral toxicity of the compounds according to the invention was determined in mice in comparison with that of the cetyl-pyridine-chloride already previously used as a standard for comparison.

The substances were administered orally to groups of 10 female mice $CF_1$ of average weight of about 20 grams, in aqueous solution and in such way that the total volume administered would be in each case 1 ml/100 g of weight.

Thus the $LD_{50}$, that is, the dose expressed in mg/kg of body weight which induces death in 50% of the animals treated with 14 days of administration was determined.

TABLE 4
ACUTE ORAL TOXICITY IN MICE EXPRESSED AS $LD_{50}$ in mg/kg.

| COMPOUNDS | $LD_{50}$ mg/kg |
| --- | --- |
| Example 1 | 910 |
| Example 2 | 1020 |
| Example 3 | 745 |
| Example 4 | 820 |
| Example 5 | 750 |
| Example 6 | 935 |
| Example 7 | 955 |
| Example 8 | 760 |
| Example 9 | 980 |
| Example 10 | 1050 |
| Example 11 | 935 |
| Example 12 | 890 |
| Cetyl pyridine chloride | 275 |

As can be seen from examination of Table 4, the oral toxicity of the substances under examination is remarkably low if it is considered that they are able to exert their sterilising activity at concentrations of the order of γ/ml or less. Also comparison with cetyl-pyridine chloride favours the compounds concerned since they appear to be about 3-4 times less toxic than the reference standard; this result assumes obvious significance when compared with the antimicrobic activity previously examined.

The cutaneous tolerance was also tested for the compounds of Examples 1, 4 and 8. The experiment was carried out on depilated rats and rabbits to which there were applied daily for a period of 30 days, pomades or suspensions in carboxymethylcellulose of the compounds under examination; these pomades and suspensions contained up to 20% of the active principle.

Neither during nor after the treatment were there observed any local reactions of an allergic or toxic nature, either acute or chronic.

Histological examination of the skin tissues which were treated did not show any particular modification.

These results therefore show that these compounds are well tolerated in vivo even in doses which are much greater than those intended for human use.

C.: IN VIVO ACTIVITY

The local activity in vivo against bacteria, mildews and yeast for the compounds described in Examples 1, 4, 8, was also tested so as to ascertain whether the activity shown by the compounds in question on cultures of micro-organisms "in vitro" is also manifested upon experimental infections "in vivo" which closely resemble the pathological conditions requiring the intervention of an antiseptic.

(a) Antibacterial activity in vivo with topical treatment

After their backs have been shaved, female $CF_1$ albino mice weighing 18-22 g are scorched (under ether anaesthetic) for 15 seconds with a pad of brass previously immersed in boiling water (7-8% of the body surface). After 90 minutes there is applied to the scorched area 0.1 ml of a suspension of Pseudomonas Aeruginosa bacteria having 15% transmittance at 650 nm. The bacterial strain in question produces a high incidence of mortality, induced by septicemic diffusion from the point of infection. After 90 minutes, with the aid of a glass rod suitably flattened at one end, the preparation containing a known concentration of the compound under examination is applied locally. The treatment is continued for a total of six days (once per day). On the fifteenth day the percentage of survivors to the tested doses in recorded.

The carrier used for applying the compounds under examination is an aqueous 0.75% solution of carboxymethyl-cellulose. The concentrations of the compounds tested are 2, 1, 0.5 and 0.25% by weight.

The results are recorded in Table 5.

TABLE 5

| SUBSTANCE | CONCENTRATION (in %) | NO. OF ANIMALS | ANIMALS DEAD ON THE 15th DAY | ANIMALS ALIVE ON THE 15th DAY | % SURVIVORS |
| --- | --- | --- | --- | --- | --- |
| Example 1 | 2 | 10 | 2 | 8 | 80 |
|  | 1 | 10 | 2 | 8 | 80 |
|  | 0.5 | 10 | 4 | 6 | 60 |
|  | 0.25 | 10 | 5 | 5 | 50 |
| Example 4 | 2 | 10 | 3 | 7 | 70 |
|  | 1 | 10 | 4 | 6 | 60 |
|  | 0.5 | 10 | 4 | 6 | 60 |
|  | 0.25 | 10 | 6 | 4 | 40 |
| Example 8 | 2 | 10 | 3 | 7 | 70 |
|  | 1 | 10 | 4 | 6 | 60 |
|  | 0.5 | 10 | 5 | 6 | 60 |
|  | 0.25 | 10 | 7 | 3 | 30 |
| Cetyl pyridine Chloride | 2 | 10 | 6 | 4 | 40 |
|  | 1 | 10 | 8 | 2 | 20 |
|  | 0.5 | 10 | 7 | 3 | 30 |
|  | 0.25 | 10 | 9 | 1 | 10 |
| Controls treated with a 0.75% solution of CMC | — | 20 | 18 | 2 | 10 |

Examination of Table 5 leads to the conclusion that the compounds under examination also have a lively antibacterial action in "vivo"; this activity is particularly marked in the case of the substance described in Example 1 which even at a concentration of 0.5% ensures a percentage of survivors which is around 50%, to reach a value of 80% for the highest dose.

In the case of cetyl pyridine chloride the correspondence between the activity in vitro and in vivo is not so secure; in fact the antibacterial action is hardly shown at a concentration of 2%, whilst at lower concentrations it is very doubtful. On the contrary the substances described in examples 1, 4, 8, ensure a secure efficacy even with other concentrations which have been considered.

(b) Topical activity upon dermatophytis from Trichophyton in cavies

Albino cavies of 250–300 g are infected, after depilation and scarification of a circular area of dorsal skin upon which there are supplied 0.1 ml of a suspension of microconidia of Trichophyton Mentagrophytes from the Pasteur Institute collection, obtained from a culture of 15 days upon Saboureaud agar. 24 Hours after infection topical treatment is started and is continued for two weeks (once per day).

The compounds to be tested are dissolved or suspended at the desired concentration, in a water-alcohol mixture (75/25 v/v) containing 0.75% by weight of carboxymethyl-cellulose (CMC). The addition of alcohol is justified by the fact that its keratolitic activity, albeit weak, is sufficient to carry the compound under examination into contact with the mycelium of the fungus which is able to penetrate below the corneal cells of the epithelium thus becoming difficult to reach. Each single application is carried out using 0.25 ml of the suspension or solution obtained as described above.

Fourteen days after infection the lesions are assessed. Assessment is carried out by attributing index numbers depending upon the seriousness of the lesions formed, as follows:
3: large scabs with ulcerations without hair growth
2: small ulcerations with desquamation of the skin and without hair growth
1: desquamation of the skin without hair growth
0: healing, with hair growth.

The results have been expressed as percentages of the average index of seriousness of infection: A.D.I. (Average Degree of Infection) of the animals treated with respect to a control group.

The substances under examination were tested at concentrations of 5 and 2.5% by weight.

The results are recorded in Table 6.

well known agent of dermatophytis which is troublesome and painful in humans and animals. Of special interest is the action of the product described in Example 1 which ensures, with the highest dose, a very high percentage of healing (nearly 90%), whilst its effect is good even with the least dose.

The said pronouncement cannot be given for cetyl pyridine chloride for which a weak activity begins to appear only with large doses.

(c) Activity upon vaginal candidiasis in mice

The treatment groups consist each of 8 female Swiss mice (Charles River CD$_1$) of average weight 20 g. The animals are infected with 0.025 ml of a 24 hour culture of *Candida albicans*, equal to $10^6$ cellules.

0.025 ml of a suspension in lanoline of the compound to be tested, at the desired concentration, are applied locally twice a day for a week, the first treatment being started five hours after infection.

The control group is treated with the lanoline alone in the same way. On the eighth day vaginal washings are carried out with 0.025 ml of sterile physiological solution, and the liquid is sown in Petri dishes containing Bacto Biggy Agon Difco as a selective growing medium for the Candida.

After 48 hours of incubation of the dishes at 30° C. a count is taken of the colonies which have grown. Assessment of the activity is quantized using the indices listed here below:
0 = 0 colonies
1 = from 1 to 10 colonies
2 = from 11 to 60 colonies
3 = from 61 to 150 colonies
4 = more than 150 colonies The results are expressed as percentages of the average index of seriousness of the infection A.D.I. (Average Degree of Infection) in the animals treated with respect to the animals in the control group.

TABLE 6

| SUBSTANCE | CONCENTRATION % by weight | NO. OF ANIMALS | EVALUATION OF SERIOUSNESS OF INFECTION (individual) | EVALUATION OF SERIOUSNESS OF INFECTION (A.D.I.) | A.D.I. % | HEALING % (100-A.D.I. %) |
|---|---|---|---|---|---|---|
| Example 1 | 5 | 6 | 0 - 1 - 1 - 0 - 0 - 0 | 0.33 | 12.36 | 87.64 |
|  | 2.5 | 6 | 1 - 1 - 1 - 1 - 0 - 1 | 0.83 | 31.09 | 68.91 |
| Example 2 | 5 | 6 | 0 - 1 - 1 - 0 - 1 - 0 | 0.50 | 18.73 | 81.27 |
|  | 2.5 | 6 | 1 - 1 - 1 - 1 - 1 1 | 1.00 | 37.45 | 62.55 |
|  | 5 | 6 | 1 - 1 - 0 - 1 - 1 - 0 | 0.67 | 25.09 | 74.91 |
|  | 2.5 | 6 | 2 - 0 - 1 - 1 - 1 - 1 | 1.00 | 37.45 | 62.55 |
| Cetyl | 5 | 6 | 1 - 2 - 1 - 0 - 2 - 2 | 1.33 | 49.81 | 50.19 |
| Pyridine | 2.5 | 6 | 2 - 1 - 2 - 3 - 3 - 2 |  | 81.27 | 18.73 |
| Controls treated only with 0.75% CMC in water-alcohol (75-15 V/V). | — | 12 | 3 - 2 - 3 - 3 - 2 - 3 3 - 3 - 2 - 2 - 3 | 2.67 | 100 | 0 |

As can be seen from Table 6, the substances described in Examples 1, 4, 8, also exert an excellent "in vivo" activity against Trichophyton Mentagrophytes, a very The substances under examination were tested at concentrations of 5 and 3% by weight.

The results are recorded in Table 7.

TABLE 7

| SUBSTANCE | CONC. % by weight | NO. OF ANIMALS | NO. OF ANIMALS SURVIVING | PROLIFERATION INDEX (Individual) | AVERAGE PROLIFERATION INDEX (A.D.I) | A.D.I. % (compared with controls) | % of healing (100-A.D.I. %) |
|---|---|---|---|---|---|---|---|
| Example 1 | 5 | 8 | 8 | 0-1-0-1-0-0-0-1 | 0.38 | 15.97 | 84.03 |
|  | 3 | 8 | 8 | 1-0-1-2-1-2-0-0 | 0.88 | 36.97 | 63.03 |
| Example 4 | 5 | 8 | 8 | 0-2-0-0-0-1-0-0- | 0.38 | 15.97 | 84.03 |
|  | 3 | 8 | 8 | 2-0-1-1-1-1--0-2 | 1.00 | 42.02 | 57.98 |
| Example 8 | 5 | 8 | 2 | 0-0-0-2-1-0-0-1 | 0.50 | 21.01 | 78.99 |
|  |  |  |  | 0-1-1-3-0-0-0-2 | 0.88 | 36.97 | 63.03 |

TABLE 7-continued

| SUBSTANCE | CONC. % by weight | NO. OF ANIMALS | NO. OF ANIMALS SURVIVING | PROLIFERATION INDEX (Individual) | AVERAGE PROLIFERATION INDEX (A.D.I) | A.D.I. % (compared with controls) | % of healing (100-A.D.I. %) |
|---|---|---|---|---|---|---|---|
| Cetyl | 5 | 8 | 2 | — | — | — | — |
| Pyridine Chloride | 3 | 8 | 6 | 2-1-3-4-2-0 | 2.00 | 84.03 | 15.97 |
| Controls treated with lanoline | — | 8 | 8 | 4-3-3-1-2-2-4-0 | 2.38 | 100.00 | 0.00 |

By examining the results recorded in Table 7 it can be seen that the products described in Examples 1, 4, 8 of the present invention are able to exert an excellent topical activity "in vivo" even against Candida albicans which is an agent of very troublesome infections, especially in women (vaginitis, vulvovaginitis, etc.). The experiment in question was also useful in showing that the products under examination are perfectly tolerated by very delicate tissues, such as, indeed, the vaginal mucous membrane, the proof of this being that all the animals treated came through the experiment without suffering any kind of trouble. The same cannot be said for cetyl pyridine chloride, which at the highest dose caused the death of 75% of the treated animals before the end of the experiment; with a lower dose mortality is reduced to 25% but, at the same time, the activity disappears, which leads to the conclusion that whereas cetyl pyridine is too toxic to have any useful application in the field of candidiasis, the substances under examination, being very active and equally well tolerated, lend themselves perfectly to use even in this sector of the infections of micro-organisms, which is certainly very important.

The compounds according to the present invention can be used with advantage in human and/or veterinary therapy, carried by suitable excipients which are acceptable from the pharmaceutical view point. For example, in infections of the oropharyngeal tract, induced by pathogenic micro-organisms, the compounds according to examples 1-12, but preferably n-decyl-dimethyl-adamantane-1-carboxyethylammonium bromide (Ex. 1), n-dodecyldimethyladamantane-1-carboxyethylammonium bromide (Ex. 4), and n-dodecyl-dimethyl-adamantane-1-carbonamidoethylammonium bromide (Ex. 8), can advantageously be administered in the form of tablets for chewing, containing from 0.5 to 2 mg of compound, or in the form of mouthwash containing from 0.25 to 1 mg of active principle per milliliter of solution.

These compounds, from what has been evidenced, lend themselves extremely well to gynaecological use, in the treatment of vaginal infections by Candida both in the form of suppositories containing 1 mg/g of active principle and in the form of washes with a concentration of between 0.1 and 1 g per liter of solution.

The quaternary ammonium salts described in the present invention can also be usefully applied locally in the case of fungoid infections of the skin and mucous membranes, in the form of powders, ointments and creams, at concentrations varying from 1 to 5% of the active principle.

The compounds in question are, moreover, recommended in the form of a solution in concentrations of between 0.5 and 2 g/liter for the disinfection of any type of wounds, cuts, burns and abrasions, or for use in hospitals for the disinfection of surgical instruments and every other type of utensil, object or surface.

Finally, they can be used as active preservatives for preventing the growth or fermentation of micro-organisms in solutions (including water and pharmaceutical preparations) or in heterogeneous phases such as foodstuffs, creams, pomades, etc., at concentrations varying from 0.0025 per thousand to other higher ones, depending upon the material to be preserved.

We claim:

1. Process for the preparation of a quaternary ammonium salt having antibacterial, fungicidal and antiprotozoic activity, comprising reacting at 5° C. to 30° C. for 12-48 hours 1-carboxy-adamantane with a compound of the formula:

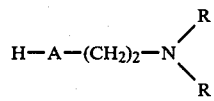

in which A is oxygen atom, R is —CH$_3$(methyl) or —C$_2$H$_5$(ethyl) group, in the presence of dicyclohexylcarbodiimide or carbonyl diimidazole as a condensing agent in anhydrous acetone as a solvent, thereby to obtain an intermediate compound:

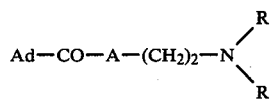

in which Ad is 1-adamantyl radical, and A and R have the meaning indicated hereinbefore, and subsequently, without isolating the intermediate compound from the reaction ambient, quaternising the compound with an alkyl halide of formula R'-X, in which:

R' represents a linear aliphatic hydrocarbon chain containing from 10 to 12 atoms of carbon, X represents a halide atom, thereby to obtain the said quaternary ammonium salt having the formula:

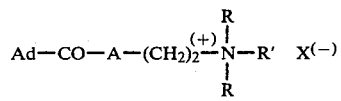

in which Ad, R, R' and X⁻ have the meanings stated above.

2. Process according to claim 1, wherein X is chlorine or bromine.

3. Process for the preparation of a quaternary ammonium salt having antibacterial, fungicidal and antiprotozoic activity, comprising reacting at 5° C. to 30°

C. for 12–48 hours 1-carboxy-adamantane with a compound of the formula:

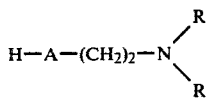

in which A is oxygen atom, R is —CH$_3$ (methyl) or —C$_2$H$_5$(ethyl) group, in the presence of dicyclohexylcarbodiimide as a condensing agent in anhydrous acetone as a solvent, thereby to obtain an intermediate compound:

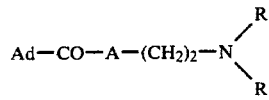

in which Ad is 1-adamantyl radical, and A and R have the meaning indicated hereinbefore and precipitated dicyclohexylurea, eliminating the dicyclohexylurea by filtration, and subsequently without isolating the intermediate compound from the reaction ambient, quaternising the compound with an alkyl halide of formula R'-X, in which:

R' represents a linear aliphatic hydrocarbon chain containing from 10 to 12 atoms of carbon, X represents a halide atom, thereby to obtain the said quaternary ammonium salt having the formula:

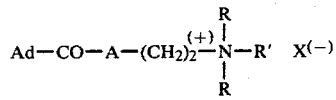

in which Ad, R, R' and X$^-$ have the meanings stated above.

* * * * *